United States Patent [19]

Fukumoto

[11] Patent Number: 5,284,049
[45] Date of Patent: Feb. 8, 1994

[54] INDENTATION HARDNESS TESTER

[75] Inventor: Mitoshi Fukumoto, Tokyo, Japan

[73] Assignee: Matsuzawa Seiki Kabushikikaisha, Tokyo, Japan

[21] Appl. No.: 865,332

[22] Filed: Apr. 8, 1992

[30] Foreign Application Priority Data

Apr. 10, 1991 [JP] Japan .................. 3-104786

[51] Int. Cl.[5] .............................. G01N 3/42
[52] U.S. Cl. ........................................ 73/82
[58] Field of Search ....................... 73/81–84; 356/378

[56] References Cited

U.S. PATENT DOCUMENTS

| 2,357,856 | 9/1944 | Tate | 73/82 |
| 3,365,937 | 1/1968 | Miserocchi | 73/81 |

FOREIGN PATENT DOCUMENTS

| 963108 | 5/1957 | Fed. Rep. of Germany. | |
| 3216729 | 11/1983 | Fed. Rep. of Germany. | |
| 0291540 | 12/1987 | Japan | 73/82 |

Primary Examiner—Robert Raevis
Attorney, Agent, or Firm—Sixbey, Friedman, Leedom & Ferguson

[57] ABSTRACT

In an indentation hardness tester a specimen placed on a specimen table is brought to a position just under an indenter mounted on one free end of a balance having its fulcrum received by a fulcrum bearing member, the balance is turned about the fulcrum by a test load to make an indentation in the specimen by the indenter and then the size of the indentation is measured through a microscope including an objective lens. The fulcrum bearing member for receiving the fulcrum of the balance is vertically movably mounted on a stationary part so that the indenter mounted on the balance is brought up from or down to a position right above the specimen table in close proximity thereto, and the microscope or at least its objective lens is pivotally mounted on the stationary part so that the objective lens turns to or turns away from a position right above the specimen table.

1 Claim, 4 Drawing Sheets

INDENTATION HARDNESS TESTER

BACKGROUND OF THE INVENTION

1. Field of the Invention

The present invention relates to an indentation hardness tester.

2. Description of the Prior Art

Heretofore there has been proposed an indentation hardness tester which will hereinbelow be described with reference to FIGS. 3 and 4.

The conventional indentation hardness tester has a case 1 as a stationary part. The case 1 has a bottom panel 2 extending horizontally, a rear panel 3 extending upwardly from the rear edge of the bottom panel 2, a lower front panel 4 extending upwardly from the front edge of the bottom panel 2 to a height shorter than that of the rear panel 3, a panel extending rearwardly from the upper edge of the lower front panel 4 and shorter than the bottom panel 2 in the front-to-back direction, a central front panel 6 extending upwardly from the rear edge of the panel 5, a panel 7 extending forwardly from the upper edge of the central front panel 6 in opposing relation to the panel 5, an upper front panel 8 extending upwardly from the front edge of the panel 7, and a top panel 9 extending between the upper edge of the upper front panel 8 and the upper edge of the rear panel 3.

Reference numeral 11 indicates a specimen table unit, which includes a vertical moving lever driver 12 which is fixedly mounted on the bottom panel 2 in the space defined by the bottom panel 2 and the panel 5 of the case 1, a vertically moving lever 13 which extends upward from the vertical moving lever driver 12 through a window 5a made in the panel 5 and is vertically moved up and down by the vertical moving lever driver 12, and a specimen table 14 mounted on the top of the vertically moving lever 13. In this instance, the specimen table 14 has a horizontal specimen bearing surface 14a on which a specimen 20 is paced from above, and the table 14 is movable back and forth with the specimen bearing surface 14a held horizontal.

Reference numeral 32 denotes a fulcrum bearing member, which is formed by a plate member which has a top surface 32a extending horizontally and a fulcrum bearing surface 32b formed by a laterally extending V-shaped groove cut in the top surface 32a, as shown in detail in FIG. 4. The fulcrum bearing member 32 is fixedly mounted on the central front panel 6.

Reference numeral 41 denotes a balance, which has a centrally-disposed downward fulcrum 42 formed by a V-shaped projecting piece which is received by the fulcrum bearing surface 32b of the fulcrum bearing member 32. The balance 41, with the fulcrum 42 received by the fulcrum bearing surface 32b of the fulcrum bearing member 32, is extended forwardly of the central front panel 6 through a window 6a made therein and carries at the extended free end an indenter 43 located close to the specimen table 14 and a test load weight 44. Further, the balance 41 is extended rearwardly in the case 1 and carries at the extended free end a horizontal balancing weight 45. The weight and position of the horizontal balancing weight 45 on the balance 41 are determined so that the balance 41 may remain level in the state in which the test load weight 44 is not mounted on the free end portion of the balance 41 near the indenter 43. The balance 41 further includes a lever 46 which extends downward from the position of the fulcrum 42 through a through hole 32c (shown in FIG. 4) made in the fulcrum bearing member 32 and by which the center of gravity of the balance 41 is located at the tip end portion of the fulcrum 42. The lever 46 carries a vertical balancing weight 47. The balance 41 further has a pin 48 planted rearwardly on the free end portion on the side opposite from the indenter 43.

Reference numeral 51 identifies a balance control, which is disposed in the case 1 between the rear panel 3 and the central front panel 6 thereof and includes an actuating lever driver 52 fixed to the rear panel 3 and an actuating lever 53 which extends upwardly from the actuating lever driver 52 and is driven up and down by the driver 52. The actuating lever 53 has in its free end portion a vertically elongated hole 54 which has loosely fitted thereinto the pin 48 of the balance 41.

Reference numeral 61 denotes a microscope which is optical means for observing the specimen 20. The microscope 61 includes an eyepiece lens 62 which is mounted on the upper front panel 8 of the case 1 in such a manner that its optical axis may extend aslant from the front of the panel 8 and into the case 1 through a window 8a made in the panel 8, an objective lens 63 which is mounted on the panel 7 of the case 1 in such a manner that its optical axis may extend vertically from under the panel 7 and into the case 1 through a window 7a made in the panel 7, and an optical system 65 which includes a reflector 64 mounted on the panel 7 in the optical path between the eyepiece lend 62 and the objective lens 63. In this instance, the objective lens 63 is mounted on the panel 7 at a position forwardly of the forward free end portion of the balance 41 so as to keep the optical path of the objective lens 63 under the panel 7 from being intercepted or blocked by the above-said free end portion of the balance 41.

With such a conventional indentation hardness tester as described above, the actuating lever 53 of the balance control 51 is normally held down by the actuating lever driver 52, and consequently, the upper inner face of the elongated hole 54 engages the pin 48 of the balance 41, causing the balance 41 to slightly turn about the fulcrum 42 received by the fulcrum bearing member 32 against a test load by the test load weight 44. On the other hand, the vertically moving lever 13 is held down by the vertically moving lever driver 12, and consequently, the specimen table 14 remains at its lowered position. Further, the specimen table 14 stays at its rear position.

When placing the specimen 20 on the specimen table 14 of the specimen table unit 11 and then actuating the vertically moving lever driver 12 of the specimen table unit 11, the vertically moving lever 13 and consequently the specimen table 14 moves up to a position where the specimen 20 lies right below the indenter 43 in adjacent but spaced relation thereto. Then, operating the actuating lever driver 52 of the balance control 51, the actuating lever 53 moves up, and hence the pin 48 of the balance 41 disengages from the elongated hole 54 of the actuating lever 53 and the balance 41 turns about the fulcrum 42 received by the fulcrum bearing member 32 owing to the test load by the test load weight 44, making an indentation in the specimen 20 by the indenter 43 with the test load based on the test load weight 44.

After an impression has been made in the specimen 20 as mentioned above, the actuating lever 53 will automatically return to its initial position when the actuating lever drive 52 of the balance control 51 is operated in a direction reverse to that in which to make the indentation in the specimen 20. As the result of this, the elongated hole 54 made in the actuating lever 53 engages the pin 48 of the balance 41 and presses it downward, by which the balance 41 is caused to turn about the fulcrum 42 received by the fulcrum bearing member 32 against the test load by the test load weight 44, thus lifting the indenter 43 off the specimen 20.

After the indenter 43 has been brought up from the indented specimen 20 as referred to above, the specimen 20 can be brought to a position just under the objective lens 63 of the microscope 61 when the specimen table 14 of the specimen table unit 11 is moved forward. Thus, the size of the indentation made in the specimen 20 can be measured by the microscope 61 through the eyepiece lens 62, the optical system 65 including the reflector 64 and the objective lens 63. Based on the thus measured size of the indentation and the test load by the test load weight 44, the hardness of the specimen 20 can be detected.

After the size of the indentation made in the specimen 20 has been measured as mentioned above, the vertically moving lever 13 will move down when the specimen table 14 is brought back to its initial position and then the vertically moving lever driver 12 is operated in a direction reverse to that in which to raise the vertically moving lever 13. Consequently, the specimen table 14 lowers to its initial position, where the specimen 20 can be removed from the table 14.

As will be seen from the above, it is possible, with the conventional indentation hardness tester of FIGS. 3 and 4, to measure the hardness of the specimen 20 on the basis of the size of the indentation made in the specimen 20 and the test load applied thereto when the indentation was made.

In the case of the conventional indentation hardness tester depicted in FIGS. 3 and 4, since the fulcrum bearing member 32 is fixedly mounted on the central front panel 6 of the case 1 which is a stationary part, and since the microscope 61 as optical means for specimen observation use, including the objective lens 63, is fixedly mounted on the case 1, the specimen 20 after being indented must be brought to a position just under the objective lens 63 of the microscope 61 by moving the specimen table 14 forward. In this case, if the specimen table 14 lies at a position where the optical axis of the objective lens 63 exactly passes through the center of the indentation made in the specimen 20, then the center of the indentation lies at the center of the visual field of the microscope 61 and the size of the indentation can be measured precisely. In practice, however, it is difficult to place the specimen 20 at a predetermined position on the specimen table 14 with high precision, and hence it is necessary to effect fine positioning control of the specimen table 14 by moving it back and forth or to right or left little by little so that the table 14 may lie at the position where the optical axis of the objective lens 63 exactly passes through the center of the indentation made in the specimen 20.

Thus, it is seriously cumbersome, in the prior art indentation hardness tester, to bring the indented specimen 20 to the position just under the objective lens 63 of the microscope 61 by moving the specimen table 14. Moreover, much skill and time are needed to bring the specimen table 14 to the above-mentioned position with high accuracy, besides it is necessary to prepare, as the specimen table 14, an expensive table which can be moved little by little.

SUMMARY OF THE INVENTION

It is therefore an object of the present invention to provide a novel indentation hardness tester which is free from the above-mentioned defects of the prior art.

The indentation hardness tester according to the present invention includes, as is the case with the prior art example shown in FIGS. 3 and 4: a specimen table which is vertically movable with respect to a stationary part; an upward fulcrum bearing member; a balance which has a downward fulcrum located centrally thereof, carries at one free end portion an indenter disposed just above the specimen table for making an indentation in a specimen and a test load weight, and carries at the other free end portion a horizontal balancing weight; and optical means for indentation observation use which includes an objective lens.

Yet, in the indentation hardness tester of the present invention, the fulcrum bearing member is mounted on the stationary part in a manner to be movable up and down so that the indenter mounted on the balance is vertically brought up from or down to a position just above the specimen table in close proximity thereto, and the optical means for indentation observation use or at least the objective lens is pivotally mounted on the stationary part so that the objective lens turns to or turns away from a position just above the specimen table.

With the indentation hardness tester of the present invention, the objective lens of the optical means is normally held at a rotational position forwardly of the position just above the specimen table. The fulcrum bearing member lies at its lowered position, and hence the balance is held at its lowered position. Further, the specimen table is also kept at its lowered position.

When placing a specimen on the specimen table and then moving up the table, the specimen can be brought into adjacent but spaced relation to the indenter mounted on the balance in the same manner as in the case of the conventional indentation hardness tester described above with respect to FIGS. 3 and 4.

After this, an indentation by the indenter can be made in the specimen when the balance is turned about the fulcrum received by the fulcrum bearing member under the test load by the test load weight.

After the balance has been a slightly turned to raise the indenter from the indented specimen, the indenter fixed to the balance can be brought up vertically from the position just above the specimen table in close proximity thereto when the fulcrum bearing member is moved up with respect to the stationary part.

Thereafter, the objective lens of the optical means can be brought to a position just above the specimen in close proximity thereto by turning the optical means or at least the objective lens with respect to the stationary part. Thus the size of the indentation made in the specimen can be measured, and the hardness of the specimen can be detected, based on the size of the indentation and the test load by the test load weight.

After the size of the indentation made in the specimen has been measured as mentioned above, the balance will automatically be brought down to its initial position when the optical means or at least the objective lens is turned to its initial position with respect to the stationary part and then the fulcrum bearing means is lowered to its initial position. Before or after this, the specimen table is moved down to its initial position, where the specimen can be removed from the specimen table.

As will be understood from the above, it is also possible, with the indentation hardness tester according to the present invention, to measure the hardness of the specimen based on the size of the indentation made in the specimen and the test load by the test load weight, as in the case of the conventional indentation hardness tester described previously in conjunction with FIGS. 3 and 4.

As referred to previously, however, in the indentation hardness tester according to the present invention, the fulcrum bearing member is vertically movably mounted on the stationary part so that the indenter carried by the balance is vertically brought up from or down to the position just above the specimen table in close proximity thereto, and the optical means or at least its objective lens is pivotally mounted on the stationary part so that the objective lens turns to or away from the position just above the specimen table.

With the above construction according to the present invention, the objective lens can be brought to the position just above the specimen where the optical axis of the objective lens is substantially aligned with the axis of the indenter at the time of making an indentation in the specimen and hence passes through the center of the indentation, simply by shifting the fulcrum bearing member upward with respect to the stationary part after the indentation of the specimen and then turning the optical means or its objective lens with respect to the stationary part. That is to say, according to the present invention, the specimen table need not be constructed movable so that it is moved forward and then subjected to fine positioning control as described previously with respect to the conventional indentation hardness tester shown in FIGS. 3 and 4. Hence, according to the present invention, the size of the indentation can be measured immediately by the optical means with high precision.

Thus, the indentation hardness tester according to the present invention permits highly accurate and easy measurement of the hardness of the specimen without involving the afore-mentioned complexity experienced in the prior art and without the necessity of employing a costly specimen table of a movable construction which calls for much skill and a large amount of time for its operation.

DESCRIPTION OF THE PREFERRED EMBODIMENT

Figure 1:
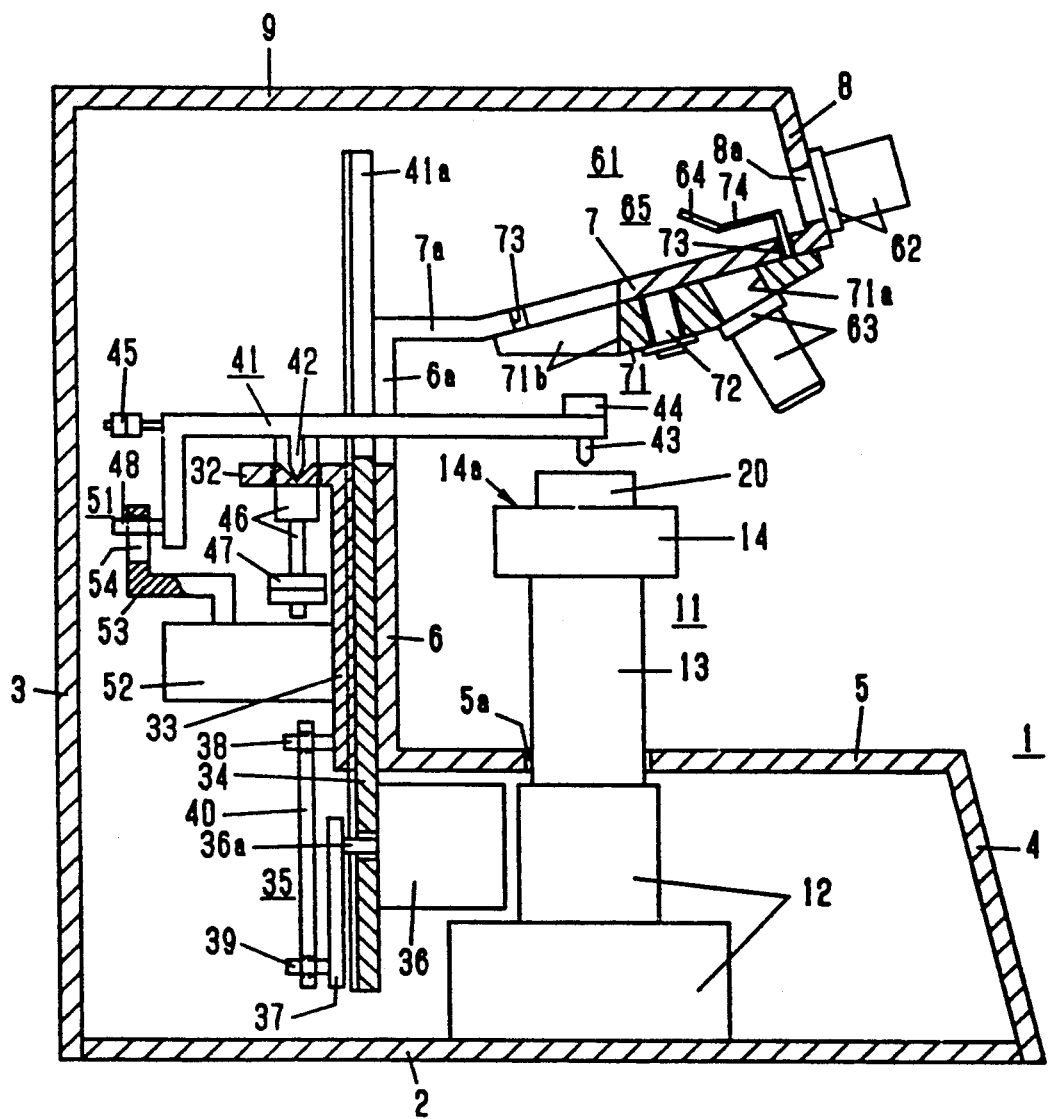
FIG. 1 is a side view, partly in section, illustrating an embodiment of the indentation hardness tester according to the present invention, with the indenter on the balance held just above the specimen table in close proximity thereto and with the objective lens held at a position outwardly of the specimen table.
Figure 2:
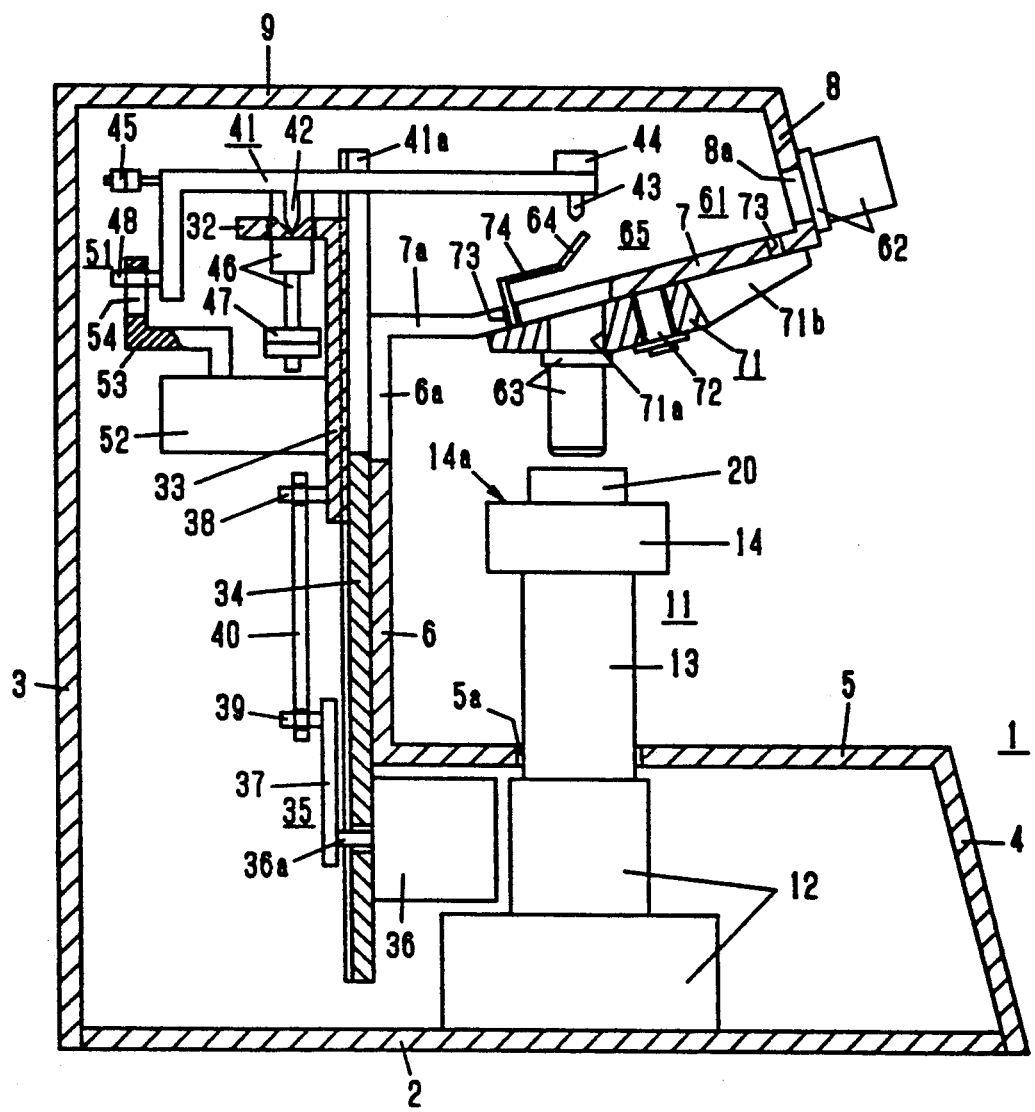
FIG. 2 is a side view, partly in section, of the FIG. 1 embodiment in a state in which the indenter on the balance is held far above the specimen table and the objective lens lies just above the specimen table.
Figure 4:
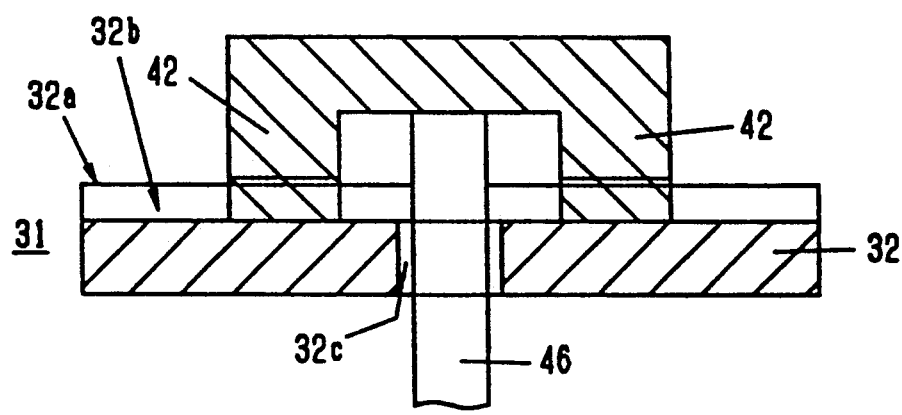
FIG. 4 is a sectional view showing the relationship between the fulcrum bearing member and the fulcrum in each of the indentation hardness testers depicted in FIGS. 1 through 3.

Referring now to FIGS. 1, 2 and 4, an embodiment of the indentation hardness tester according to the present invention will be described.

Figure 3:
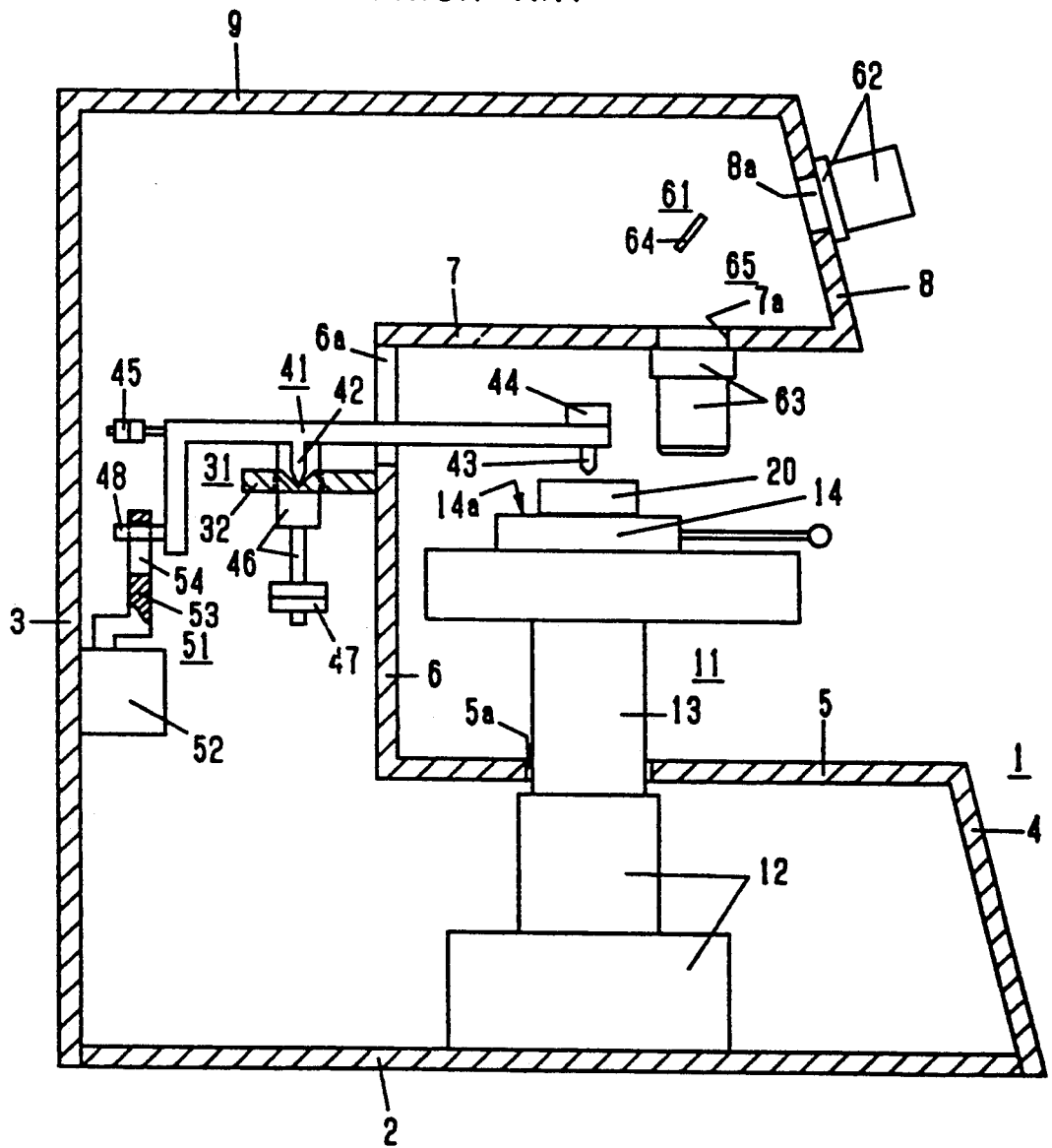
FIG. 3 is a side view, partly in section, schematically showing a conventional indentation hardness tester.

In FIGS. 1 and 2 the parts corresponding to those in FIG. 3 are identified by the same reference numerals and no detailed description will be given of them.

The indentation hardness tester illustrated in FIGS. 1, 2 and 4 is identical in construction with the prior art example of FIGS. 3 and 4 except in such points as mentioned below.

The indentation hardness tester of the present invention has a movable plate 33, which is mounted on a movable plate guide member 34 fixedly mounted on the central front panel 6 of the case 1. The movable plate 33 is vertically movable but its horizontal or lateral movement is limited by the guide 34. The movable plate 33 has the fulcrum bearing member 32 extending rearwardly from the upper end portion of the plate 33 at right angles thereto and a pin 38 extending rearwardly from the lower end portion of the plate 33 at right angles thereto.

The indentation hardness tester of the present invention further includes a movable plate driver 35, which comprises a motor 36 fixedly mounted on the lower portion of the movable plate guide 34, a rotary arm 37 fixed at one end to a motor shaft 36a, a pin 39 planted on the other end of the rotary arm 37 and a coupling lever 40 pivotally secured at both ends to the pin 38 of the movable plate 33 and the pin 39 of the rotary arm 37, respectively.

The actuating lever driver 52 of the balance control 51 is fixedly mounted on the movable plate 33. The panel 7 of the case 1 has a window 7a through which the balance 41 can be moved up and down. The movable plate guide 34 has a window 41a which permits vertical movement of the balance 41.

On the outside of the panel 7 of the case 1 there is pivotally mounted about a shaft 72 planted on the panel 7 a rotary disc 71 which has a through hole 71a and a notch 71b. The objective lens 63 is fixedly mounted on the rotary disc 71 at the position of the through hole 71a from below. The panel 7 has a slit 73 circular about the shaft 72 and the rotary disc 71 has secured thereto a support lever 74 extending into the case 1 through the slit 73 and carrying the reflector 64 at its free end. In this instance, the slit 73 is formed so that when the rotary disc 71 has been turned to a position where the support lever 74 abuts against one end of the slit 73, the optical axis of the objective lens 63 passes through the center of the top surface 14a of the specimen table 14 and so that when the rotary disc 71 has been turned around 180 degrees from the above-said position, the objective lens 63 lies forwardly of the position just above the specimen table 14.

With such an indentation hardness tester of the present invention, the rotary disc 71 normally lies at the rotational angular position where the objective lens 63 stays forwardly of the specimen table 14 as shown in FIG. 1. In this case, the movable plate 33 has been lowered by the movable plate driver 35 to its lowered position, and hence the fulcrum bearing member 32 is held at its lowered position. Moreover, as is the case with the prior art example of FIGS. 3 and 4, the actuating lever 53 of the balance control 51 has been retreated downward by the actuating lever driver 52 to the position where the upper inner face of the elongated hole 54 of the actuating lever 53 receives the pin 48 of the balance 41, hence the balance 41 has slightly turned, from its level state, about the fulcrum 42 received by the fulcrum bearing member 32 against the test load by the test load weight 44. The vertically moving lever 13 of the specimen table unit 11 has also been lowered by the vertically moving lever driver 12 to its lowered position, and consequently, the specimen table 14 is held at its lowered position.

By actuating the vertically moving lever driver 12 after placing the specimen 20 on the specimen table 14, the vertically moving lever 13 ascends and consequently the specimen table 14 moves up, bringing the specimen 20 into adjacent but spaced relation to the indenter 43.

By activating the actuating lever driver 52 of the balance control 51 after the above-mentioned operation, the actuating lever 53 is raised to thereby disengage the pin 48 of the balance 41 from the upper inner face of the elongated hole 54 of the actuating lever 53. In consequence, the balance 41 is turned about the fulcrum 42 under the test load by the test load weight 44, by which an indentation can be made in the specimen 20 by the indenter 43.

After the indentation has thus been made in the specimen 20, the actuating lever 53 will return to its initial position when the actuating lever driver 52 of the balance control 51 is operated in a direction reverse to that for making the indentation. As the result of this, the elongated hole 54 made in the actuating lever 53 engages the pin 48 of the balance 41 and presses it downward, by which the balance 41 turns about the fulcrum 42 received by the fulcrum bearing member 32 against the test load by the weight 44. Thus, the indenter 43 can be lifted off the specimen 20.

By putting the motor 36 of the movable plate driver 35 after the above operation, the movable plate 33 is guided up by the movable plate guide 34 through the rotary arm 37 and the coupling lever 40, and consequently, the balance 41 ascends together with the balance control 51 accordingly, as shown in FIG. 2. In this way, the indenter 43 carried by the balance 41 can be further brought up vertically to a higher position.

Then, by turning the rotary disc 71 until the support lever 74 planted thereon comes into contact with one end of the slit 73 cut in the panel 7, the objective lens 63 of the microscope 61 can be brought to a position right above specimen 20, and at this time, the optical axis of the objective lens 63 can be brought into alignment with the optical axis of the eyepiece lens 62 via the reflector 64. Hence, the size of the indentation made in the specimen 20 can be measured by the microscope 61 through the eyepiece lens 62, the optical system 65 including the reflector 64 and the objective lens 63. Thus, the hardness of the specimen 20 be detected on the basis of the size of the indentation and the test load by the weight 44.

By turning the rotary disc 71 back to its initial position and operating the movable plate driver 35 to lower the movable plate 33 after the measurement of the size of the indentation, the fulcrum bearing member 32 descends together with the balance 41. Before or after this, the vertically moving lever driver 12 of the specimen table unit 11 is operated to lower the vertically moving lever 13 until the specimen 20 on the specimen table 14 is brought down to its initial position, where it can be removed from the table 14.

As will be appreciated from the above, the indentation hardness tester according to the present invention, shown in FIGS. 1, 2 and 4, also permits the measurement of the hardness of the specimen 20 on the basis of the size of the indentation made therein and the test load applied when the indentation was made, as is the case with the prior art example depicted in FIGS. 3 and 4.

It must be noted here, however, that the indentation hardness tester of the present invention has a construction in which the fulcrum bearing member 32 is mounted on the case 1 in a manner to be movable up and down so that the indenter carried by the balance 41 can be vertically brought up from or down to the position just above the specimen table 14 in close proximity thereto and the objective lens 63 of the microscope 61 is pivotally mounted on the case 1 so that the objective lens 63 can turn to or away from the position right above the specimen table 14. With such a construction, after the indentation has been made in the specimen 20, the optical axis of the objective lens 63 can be brought into alignment with the axis of the indenter 43 when the latter was pressed into the specimen 20, and hence can be made to pass through the center of the indentation, simply by moving up the movable plate 33 along the movable plate guide 34 by the movable plate driver 35 relative to the case 1 and then turning the objective lens 63 via the rotary disc 71 relative to the case 1, without the necessity of moving forward the specimen table 14 and then positioning it through fine positioning control as in the conventional indentation hardness tester described previously in respect of FIGS. 3 and 4. Thus, the size of the indentation can be immediately measured with high accuracy.

As will be seen from the above, the indentation hardness tester according to the present invention, shown in FIGS. 1, 2 and 4, makes it possible to measure the hardness of the specimen 20 with high accuracy without involving the afore-mentioned troublesomeness encountered in the prior art and without calling for much skill, a large amount of time and an expensive specimen table of the movable mechanism.

While in the above only the objective lens 63 has been described to be movable relative to the case 1, the microscope 61 can be made movable in its entirety relative to the case 1.

While one embodiment of the present invention has been illustrated and described it is to be understood that it was merely for the purpose of explanation. It will be apparent to those skilled in the art that many modifications and variations of the invention may be effected without departing from the scope of the novel concepts of the invention.

What is claimed is:

1. An indentation hardness tester comprising:
   a specimen table for placing thereon a specimen, which is vertically movable with respect to a stationary part;
   an upward fulcrum bearing member;
   a balance which has a downward fulcrum located centrally thereof, carries at one free end portion an indenter disposed just above said specimen table for making an indentation in said specimen and a test load weight, and carries a horizontal balancing weight at the other free end portion; and
   optical means for indentation observation use, said optical means including an objective lens;
   wherein said fulcrum bearing member is vertically movably mounted on said stationary part so that said indenter mounted on said balance is vertically brought up from or down to a position right above said specimen table in close proximity thereto; and wherein said optical means or at least said objective lens is pivotally mounted on said stationary part so that said objective lens turns to or turn away from a position right above said specimen table.

* * * * *